United States Patent
Oberdorf et al.

(10) Patent No.: US 6,310,071 B1
(45) Date of Patent: Oct. 30, 2001

(54) 2-(O-(PYRIMIDIN-4-YL)METHYLENEOXY) PHENYLACETIC ACID DERIVATIVES AND THEIR USE FOR CONTROLLING HARMFUL FUNGI AND ANIMAL PESTS

(75) Inventors: Klaus Oberdorf, Heidelberg; Wassilios Grammenos, Ludwigshafen; Hubert Sauter, Mannheim; Thomas Grote, Schifferstadt; Reinhard Kirstgen, Neustadt; Ruth Müller, Friedelsheim; Bernd Müller, Frankenthal; Franz Röhl, Schifferstadt; Michael Rack, Heidelberg; Herbert Bayer, Mannheim; Gisela Lorenz, Hambach; Eberhard Ammermann, Heppenheim; Siegfried Strathmann, Limburgerhof; Volker Harries, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/604,111

(22) Filed: Jun. 26, 2000

Related U.S. Application Data

(62) Division of application No. 09/077,359, filed as application No. PCT/EP96/05523 on Dec. 11, 1996, now Pat. No. 6,114,342.

(30) Foreign Application Priority Data

Dec. 19, 1995 (DE) ................................. 195446699
May 21, 1996 (DE) ............................... 196 20 392

(51) Int. Cl.$^7$ ..................... A01N 43/54; C07D 239/26; C07D 239/30; C07D 239/34
(52) U.S. Cl. ..................... 514/269; 514/272; 544/296; 544/298; 544/316; 544/330
(58) Field of Search ................... 544/296, 298, 544/316, 330; 514/269, 272

(56) References Cited

U.S. PATENT DOCUMENTS 5,334,577 * 8/1994 Wenderoth et al. ............... 546/286
5,371,222 * 12/1994 Hayase et al. ..................... 544/316

FOREIGN PATENT DOCUMENTS 0 254 426 * 1/1988 (EP) .

* cited by examiner

*Primary Examiner*—Richard L. Raymond
*Assistant Examiner*—Venkataraman Balasubramanian
(74) *Attorney, Agent, or Firm*—Keil & Weinkauf

(57) ABSTRACT

2-(O-[pyrimidin-4-yl]methylenoxy)phenylacetic acid derivatives of the general formula I

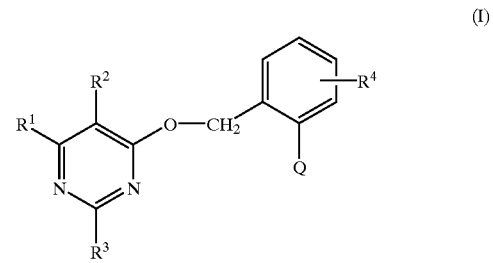

(I)

and the salts and N-oxides thereof where the radicals $R^1$ to $R^4$ and Q have the following meanings:

$R^1$ is hydrogen or alkyl;

$R^2$ is halogen, alkyl or haloalkyl;

$R^3$ is hydrogen; amino; hydroxyl; mercapto; halogen; unsubstituted or phenyl-substituted alkyl; haloalkyl; alkoxyalkyl; alkoxy; monoalkylamino; dialkylamino; alkylthio; alkylsulfoxyl; alkylsulfonyl; cycloalkyl; trialkylsilyloxy, or: phenyl, phenoxy, phenoxymethyl, benzyloxy or hetaryl, unsubstituted or substituted in the aromatic ring;

$R^4$ is hydrogen; cyano; halogen; alkyl; haloalkyl or alkoxy;

Q is
$C(=NOCH_3)$—$CONHCH_3$,
$C(=NOCH_3)$—$COOCH_3$ or
$N(OCH_3)$—$COOCH_3$, the salts and N-oxides thereof, and their use for controlling harmful fungi and animal pests.

19 Claims, No Drawings

2-(0-(PYRIMIDIN-4-YL)METHYLENEOXY) PHENYLACETIC ACID DERIVATIVES AND THEIR USE FOR CONTROLLING HARMFUL FUNGI AND ANIMAL PESTS

This is a Divisional Application of application Ser. No. 09/077,359, filed on May 28, 1998 now U.S. Pat. No. 6,114,342, (allowed) which is a National Stage Application under 35 U.S.C. 371, of International Application No. PCT/EP 96/05,523, filed Dec. 11, 1996.

The present invention relates to 2-(O-[pyrimidin-4-yl]methyleneoxy)phenylacetic acid derivatives of the general formula I

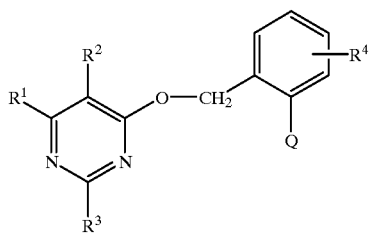

and the salts and N-oxides thereof where the radicals $R^1$ to $R^4$ and Q have the following meanings:

$R^1$ is hydrogen or $C_1$–$C_4$-alkyl;

$R^2$ is halogen, $C_1$–$C_2$-alkyl or $C_1$–$C_2$-haloalkyl;

$R^3$ is hydrogen; amino; hydroxyl; mercapto; halogen; $C_1$–$C_8$-alkyl, it being possible for the alkyl radicals to have attached to them a phenyl group which, in turn, can have attached to it one or, independently of one another, two of the following substituents: halogen, cyano, nitro, $C_1$–$C_4$-alkyl, $C_1$–$C_4$-haloalkyl and $C_1$–$C_4$-alkoxy; $C_1$–$C_8$-haloalkyl; $C_1$–$C_8$-alkoxy-$C_1$–$C_4$-alkyl; $C_1$–$C_8$-alkoxy; $C_1$–$C_8$-monoalkylamino; di-$C_1$–$C_8$-alkylamino; $C_1$–$C_8$-alkylthio; $C_1$–$C_8$-alkylsulfoxyl; $C_1$–$C_8$-alkylsulfonyl; $C_3$–$C_8$-cycloalkyl; tri-$C_1$–$C_8$-alkylsilyloxy or the following, unsubstituted or substituted in the aromatic ring: phenyl, phenoxy, phenoxymethyl, benzyloxy or hetaryl;

$R^4$ is hydrogen; cyano; halogen; $C_1$–$C_4$-alkyl; $C_1$–$C_4$-haloalkyl or $C_1$–$C_4$-alkoxy;

Q is
  C(=NOCH$_3$)—CONHCH$_3$,
  C(=NOCH$_3$)—COOCH$_3$ or
  N(OCH$_3$)—COOCH$_3$.

In addition, the invention relates to compositions comprising the compounds I and to their use for controlling harmful fungi and animal pests.

Fungicidally and/or insecticidally and acaricidally active methyl α-[2-(heteroaryloxymethylene)phenyl]-α-methoxyiminoacetamides have been disclosed (EP-A 398 629; EP-A 477 631; JP-A 04/182 461; German Patent Application File Ref. No. 1 95 26 661.7).

Furthermore, fungicidally and/or insecticidally and acaricidally active methyl α-[2-(heteroaryloxymethylene) phenyl]-α-methoxyiminoacetates have been disclosed (cf. EP-A 254 426, EP-A 363 818, EP-A 407 873).

In addition, fungicidally and/or insecticidally and acaricidally active methyl N-[2-(heteraryloxymethylene)phenyl]-N-methoxycarbamates have been disclosed (cf. WO-A 93/15046).

The activity of the compounds described in the above-mentioned publications is as yet unsatisfactory.

It is an object of the invention to provide novel compounds which have improved properties in the control of harmful fungi and animal pests.

We have found that this object is achieved by the compounds I defined at the outset, by compositions comprising them and by their use for controlling harmful fungi and animal pests.

The compounds I are prepared by methods similar to those described in the literature mentioned at the outset.

When synthesizing the compounds I, it is generally irrelevant whether the group Q or the 2-(O-[pyrimidin-4-yl]-methyleneoxy) group is synthesized first.

For example, the compounds I are obtained by reacting a pyrimidin-4-ol of the formula II with a benzyl derivative of the formula III in a manner known per se in an inert organic solvent in the presence of a base.

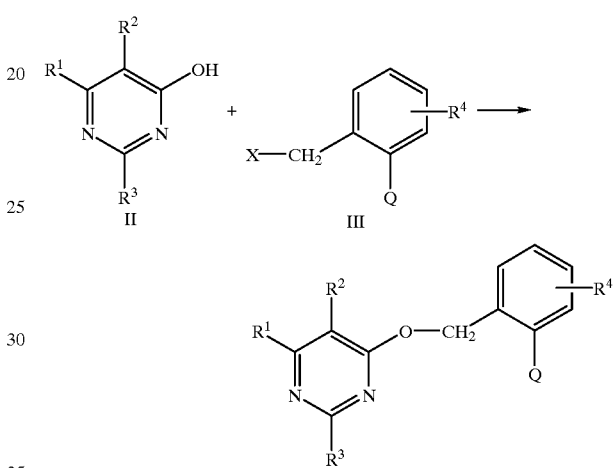

(Q = C(=NOCH$_3$)—CONHCH$_3$), C(=NOCH$_3$)—COOCH$_3$ or N(OCH$_3$)—COOCH$_3$)

In formula III, X is a nucleophilically exchangeable leaving group such as halogen (eg. chlorine, bromine or iodine), alkylsulfonyl (eg. methylsulfonyl or trifluoromethylsulfonyl) or arylsulfonyl (eg. [phenylsulfonyl or 4-methylphenylsulfonyl).

The reaction is normally carried out at from 0 to 80, preferably from 20 to 60° C.

Suitable solvents are aromatic hydrocarbons such as toluene, o-, m- and p-xylene, halogated hydrocarbons such as methylene chloride, chloroform and chlorobenzene, ethers such as diethyl ether, duisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol, ketones such as acetone and methyl ethyl ketone, and also dimethyl sulfoxide, dimethyl formamide, dimethylacetamide, 1,3-dimethylimidazolidin-2-one and 1,3-dimethyltetrahydro-2(1H)-pyrimidinone. Especially preferred are methylene chloride, acetone and dimethylformamide.

Mixtures of these can also be used.

Suitable bases are, generally, inorganic compounds with basic character such as alkali metal and alkaline earth metal hydroxides such as lithium hydroxide, sodium hydroxide, potassium hydroxide, calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as potassium carbonate and calcium carbonate, and alkali metal hydrogen carbonates such as potassium hydrogen carbonate and calcium hydrogen carbonate and alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride, and alkali metal and alkaline earth metal alkoxides such as sodium methoxide, potassium ethoxide, potassium tert-butoxide and dimethoxymagnesium.

Furthermore suitable as bases are organic bases, for example tertiary amines such as trimethylamine, triethylamine, diisopropylethylamine and N-methylpiperidine, pyridine, substituted pyridines such as collidine, lutidine and 4-dimethylaminopyridine, and bicyclic amines.

Especially preferred are sodium hydroxide, sodium hydride, potassium carbonate and potassium tert-butoxide.

The bases are generally used in equimolar amounts or in an excess or else, if desired, as the solvent.

It may be advantageous for the reaction to add a catalytic amount of a crown ether, for example 18-crown-6 or 15-crown-5.

The reaction can also be carried out in two-phase systems composed of, for example, a solution of alkali metal or alkaline earth metal hydroxides or alkali metal or alkaline earth metal carbonates in water and an organic phase, for example halogenated hydrocarbons. Phase-transfer catalysts which can be added are ammonium halides and ammonium tetrafluoroborates, eg. benzyltriethylammonium chloride, benzyltributylammonium bromide, tetrabutylammonium chloride, hexadecyltrimethylammonium bromide or tetrabutylammonium tetrafluoroborate, and phosphonium halides such as tetrabutylphosphonium chloride or tetraphenylphosphonium bromide.

It may be advantageous for the reaction first to treat the compounds II with base and to react the resulting salt with the compounds III.

The compounds II can be obtained by subjecting β-ketoesters VI to a condensation reaction with amidines, guanidines, ureas or thioureas VII by methods similar to known processes [cf. J. Chem. Soc. (1946), page 5].

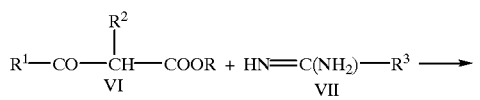

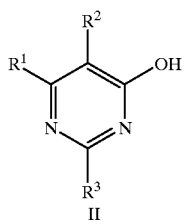

R in formula VI is mainly a $C_1$–$C_4$-alkyl group, in particular methyl or ethyl.

The reaction is normally carried out at from 0 to 120, preferably 20 from 20 to 80,° C. and in particular at the boiling point of the solvent. Solvents which are normally used are alcohols, in particular methanol or ethanol.

The compounds VII can also be employed in the form of their salts, in particular as the hydrohalides (eg. hydrochloride or hydrobromide). If salts are used, it is expedient to carry out the reaction in the presence of a base (eg. alkaline earth metal or alkali metal alkoxides, or alkaline earth metal or alkali metal hydroxides, eg. sodium methoxide, sodium ethoxide, potassium tert-butoxide, sodium hydroxide, potassium hydroxide and calcium hydroxide).

The starting compounds of type II and their syntheses are generally known, in particular from the following publications:

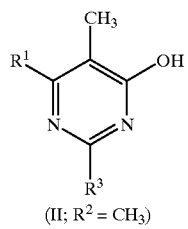

Justus Liebigs Ann. Chem. 758, (1972), pages 125, 127, 130;
Chem. Pharm. Bull. 22, (1974), pages 1239, 1240, 1245–1247;
J. Amer. Chem. Soc. 79 (1957) page 2230;
Bull. Soc. Chim. Fr. (1965), pages 2301–2306;
Bull. Soc. Chim. Fr. (1963), page 673;
BE-A 645062;
Recl. Trav. Chim. Pays-Bas 87, 10, (1968), page 1089;
Chem. Pharm. Bull. 36, 5, (1988), pages 1669–1675;
Tetrahedron 25, (1969), pages 5989, 5992;
J. Org. Chem. 35, (1970), pages 3786, 3790, 3791;
Z. Chem., GE 25, 9, (1985), pages 328–329;
J. Chem. Soc. (1950), pages 452, 456, 458;
Am. Chem. J. 29 (1903), page 487;
Bull. Soc. Chim. Belg. 68 (1959), pages 30, 40;
J. Biol Chem. 3 (1907), page 303;
Arch. Pharm. (Weinheim Ger.) GE, 317, 5, (1984), pages 425–430;
Am. Chem. J. 31 (1904), page 595;
Am. Chem. J. 43 (1910), page 23;
J. Amer. Chem. Soc. 51 (1929), page 1240;
Am. Chem. J. 42 (1909), page 368;
Rocz. Chem. 51, (1977), pages 1227, 1228, 1230;
Pol. J. Chem. EN, 55, 7/8, (1981), pages 1673–1676;
Org. Mass Spectrom. 14, (1979), pages 405, 409, 412;
Aust. J. Chem. 41, 8, 1988, 1209–1219;
Pol. J. Chem. 57, 7–9, (1983), pages 1027–1031;

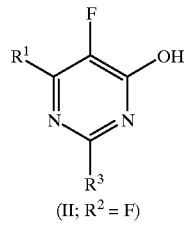

CS-A 107166;
BE-A 627342;
U.S. Pat. No. 3,954,759;
U.S. Pat. No. 3,954,758;
CS-A 108806;
SU-A 232975;
BE-A 860309;
JP-A 50150936;

Gazz. Chim. Ital. 93 (1963) pages 1268, 1272;
Collect. Czech. Chem. Commun. 27 (1962) pages 2250–2560;
J. Med. Chem. 8 (1965), page 253;
J. Org. Chem. 27 (1962), page 2580;
J. Chem. Soc. C. (1967), page 1822;
J. Chem. Soc. C. (1967), pages 2206–2207;
J. Med. Chem. 36, 18 (1993), pages 2627–2638;
J. Chem. Soc. (1959), pages 3278, 3284;
J. Am. Chem. Soc. 79 (1957), page 4559;
Acta Chem. Scand. 23 (1969), page 294.

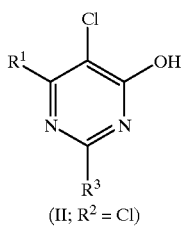

(II; $R^2$ = Cl)

BE-A 645062;
GB-A 1174165;
Collect. Czech. Chem. Commun. 27 (1962), pages 2250–2560;
J. Org. Chem. 27 (1962), pages 3507, 3510;
J. Med. Chem. 6 (1963), pages 688–693;
J. Med. Chem. 36, 18 (1993), pages 2627–2638.

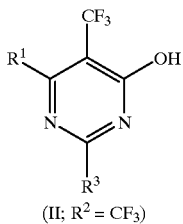

(II; $R^2$ = $CF_3$)

Heterocycles 31, 3 (1990), pages 569–574.

The starting compounds III.1 (X=Cl) and III.2 (X=Br) in which Q is C(=NOCH$_3$)—CONHCH$_3$,—cf. EP-A 477 631, Table 1, No. 332 and 333—are prepared successfully from the corresponding alkoxy, or aryloxy, compounds VII

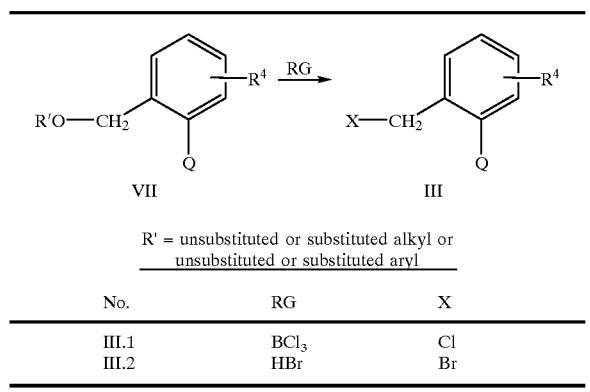

R' = unsubstituted or substituted alkyl or unsubstituted or substituted aryl

| No. | RG | X |
|---|---|---|
| III.1 | BCl$_3$ | Cl |
| III.2 | HBr | Br | by means of cleavage with, for example, boron trichloride (for III.1) or hydrogen bromide (for III.2) in inert solvents such as halogenated hydrocarbons at from (−30) to 40° C. An advantageous synthesis from the corresponding compound VII where R'=2-tolyl (see EP-A 477 631, Table 1, No. 94) is described in Examples 1 to 3.

The preparation of the compounds III where Q is C(=NOCH$_3$)—COOCH$_3$ has been disclosed in EP-A 363 818.

The preparation of the compounds III where Q is N(OCH$_3$)—COOCH$_3$ has been disclosed in WO-A 93/15046.

Upon preparation, the compounds I can be obtained in the form of E/Z isomer mixtures, due to their C=N double bonds in group Q, and these isomer mixtures can be separated into the individual compounds in the customary manner, for example by crystallization or chromatography.

However, if isomer mixtures are obtained upon synthesis, it is generally not absolutely necessary to separate the isomers since in some cases the individual isomers may be converted into each other during preparation for use, or upon use (for example when exposed to light, acids or bases). Similar conversions can also take place after application, for example in the treatment of plants within the treated plants or within the harmful fungus or animal pest to be controlled.

In relation to the C=N double bond in group Q, the E isomers of the compounds I are preferred with a view to their activity (configuration based on the OCH$_3$ group relative to the —CONHCH$_3$ or —COOCH$_3$ group).

Also part of the invention are the salts of the acid-resistant compounds I which contain basic centers, mainly basic nitrogen atoms, in particular with mineral acids such as sulfuric acid and phosphoric acid, or Lewis acids such as zinc chloride. The nature of the salt is normally irrelevant. Preferred for the purposes of the invention are those salts which do not damage the plants, areas, materials or spaces to be kept free from harmful fungi or animal pests, and which do not adversely affect the activity of the compounds I. Especially important are those salts which are suitable for agricultural purposes.

The salts of the compounds I are accessible in a manner known per se, mainly by reacting the corresponding compounds I with the abovementioned acids in water or an inert organic solvent at from (−80) to 120, preferably 0 to 60, ° C.

The compounds of the formula I can also be converted into their N-oxides, either by known methods or by similar processes {cf., for example, A. Albini and S. Pietra, Heterocyclic N-Oxides, CRC-Press Inc., Boca Raton, USA 1991; H. S. Mosher et al., Org. Synth. Coll. Vol. IV, 1963, page 828; E. C. Taylor et al., Org. Synth. Coll. Vol. IV, 1963, page 704; T. W. Bell et. al., Synth. 69, 226 (1990)}.

Amongst the oxidants conventionally used for oxidizing the pyridine ring, examples which may be mentioned are peracetic acid, trifluoroperacetic acid, perbenzoic acid, m-chloroperbenzoic acid, monopermaleic acid, magnesium monoperphthalate, sodium perborate, Oxone® (contains peroxodisulfate), pertungstic acid and hydrogen peroxide.

Examples of suitable solvents are water, sulfuric acid, carboxylic acids such as acetic acid and trifluoroacetic acid, and halogenated hydrocarbons such as dichloromethane and chloroform.

The oxidation is normally successfully carried out at from 0° C. to the boiling point of the reaction mixture.

The oxidant is normally employed in at least equimolar amounts based on the starting compound. However, a large excess of oxidant has generally proved to be especially advantageous.

Collective terms which generally represent the groups which follow were used in the definitions of the compounds I given at the outset:

Halogen: fluorine, chlorine, bromine and iodine;

Alkyl: straight-chain or branched alkyl groups having 1 to 4, 6 or 8 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Alkylamino: an amino group which has attached to it a straight-chain or branched alkyl group having 1 to 6 carbon atoms as mentioned above;

Dialkylamino: an amino group which has attached to it two independent straight-chain or branched alkyl groups having in each case 1 to 6 carbon atoms as mentioned above;

Alkylsulfoxyl: eg. $C_1$–$C_8$-alkylsulfoxyl: alkyl groups as defined above which are bonded to the skeleton via a sulfoxyl group (—SO—);

Alkylsulfonyl: eg. $C_1$–$C_8$-alkylsulfonyl alkyl groups as defined above which are bonded to the skeleton via a sulfonyl group (—SO$_2$—);

trialkylsilyloxy: eg. tri-$C_1$–$C_8$-alkylsilyloxy: silyloxy groups

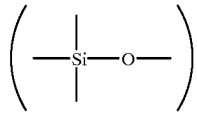

which have attached to the silicon atom three alkyl groups as defined above and which are bonded to the skeleton via the oxygen atom;

Haloalkyl: straight-chain or branched alkyl groups having 1 to 6 carbon atoms, it being possible for some or all of the hydrogen atoms of these groups to be replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluorimethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 4, 6 or 8 carbon atoms as mentioned above which are bonded to the skeleton via an oxygen atom (—O—), eg. $C_1$–$C_6$-alkoxy such as methyloxy, ethyloxy, propyloxy, 1-methylethyloxy, butyloxy, 1-methylpropyloxy, 2-methylpropyloxy, 1,1-dimethylethyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy;

Alkoxyalkyl: eg. $C_1$–$C_8$-alkoxy-$C_1$–$C_4$-alkyl: alkyl groups having 1 to 4 carbon atoms as defined above which have attached to them an alkoxy group having 1 to 8 carbon atoms as mentioned above;

Alkylenedioxy: eg. $C_1$–$C_2$-alkylenedioxy: straight-chain or branched alkylene groups having 1 to 2 carbon atoms which are incorporated into, or bonded to, the skeleton in two positions via in each case one oxygen atom (—O—) such as methylenedioxy (—O—CH$_2$—O—) or ethylenedioxy (—O—CH$_2$CH$_2$—O—);

Alkylthio: straight-chain or branched alkyl groups having 1 to 4 or 6 carbon atoms as mentioned above which are bonded to the skeleton via a sulfur atom (—S—), eg. $C_1$–$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

Cycloalkyl: eg. $C_3$–$C_8$-cycloalkyl: monocyclic alkyl groups having 3 to 8 carbon ring members, eg. cyclopropyl, cyclobutyl, cyclopentyl and cyclohexyl;

Heteroaryl: aromatic mono- or polycyclic radicals which additionally contain, beside carbon ring members, one to four nitrogen atoms or one to three nitrogen atoms and one oxygen or one sulfur atom or one oxygen or one sulfur atom, eg.

5-membered heteroaryl containing one to three nitrogen atoms: 5-membered heteroaryl ring groups which contain, beside carbon atoms, one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered heteroaryl containing one to four nitrogen atoms or one to three nitrogen atoms and one sulfur or oxygen atom or one oxygen or one sulfur atom: 5-membered heteroaryl ring groups which, beside carbon atoms, contain, as ring members, one to four nitrogen atoms or one to three nitrogen atoms and one sulfur or oxygen atom or one oxygen or sulfur atom, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered heteroaryl containing one to three nitrogen atoms or one nitrogen atom and/or one oxygen or sulfur atom: 5-membered heteroaryl ring groups which contain, beside carbon atoms, one to four nitrogen atoms or one to three nitrogen atoms and one sulfur or oxygen atom or one oxygen or one sulfur atom as ring members and in which two adjacent carbon ring members or one nitrogen and an adjacent carbon ring member are bridged by a buta-1,3-diene-1,4-diyl group;

5-membered heteroaryl, bonded via nitrogen and containing one to four nitrogen atoms, or benzo-fused 5-membered heteroaryl bonded via nitrogen and containing one to three nitrogen atoms: 5-membered heteroaryl ring groups which contain, besides carbon atoms, one to four nitrogen atoms, or one to three nitrogen atoms, as ring members and in which two adjacent carbon ring members or one nitrogen and an adjacent carbon ring member are bridged by a buta-1, 3-diene-1,4-diyl group, these rings being bonded to the skeleton via one of the nitrogen ring members;

6-membered heteroaryl containing one to three, or one to four, nitrogen atoms: 6-membered heteroaryl ring groups which, besides carbon atoms, contain one to three, or one to four, nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered heteroaryl, containing one to four nitrogen atoms: 6-membered heteroaryl ring groups in which two adjacent carbon ring members are bridged by a buta-1,3-diene-1,4-diyl group, eg. quinoline, isoquinoline, quinazoline and quinoxaline.

The term "partially or fully halogenated" is intended to express that in groups characterized thus some or all of the hydrogen atoms can be replaced by identical or different halogen atoms as mentioned above.

The term "unsubstituted or substituted" is intended to express that in groups characterized thus some or all of the hydrogen atoms can be replaced by identical or different groups, for example those which have been mentioned under the collective terms given above.

Preferred with a view to their biological activity against harmful fungi and animal pests are those compounds I where the radicals have the following meanings, alone or in combination:

$R^1$ is hydrogen;
$R^1$ is methyl;
$R^2$ is halogen, in particular fluorine and chlorine;
$R^2$ is methyl;
$R^2$ is trifluoromethyl;
$R^3$ is $C_1$–$C_8$-alkyl, it being possible for this radical to be partially or fully halogenated;
$R^3$ is $C_3$–$C_6$-cycloalkyl;
$R^3$ is $C_1$–$C_8$-alkoxy;
$R^3$ is $C_1$–$C_8$-alkylthio;
$R^3$ is di-$C_1$–$C_8$-alkylamino;
$R^3$ is $C_1$–$C_8$-alkylsulfoxyl;
$R^3$ is $C_1$–$C_8$-alkylsulfonyl;
$R^3$ is chlorine;
$R^3$ is phenyl, it being possible for this radical to have attached to it one to three of the following groups: halogen, $C_1$–$C_4$-alkyl, cyano, $C_1$–$C_4$-alkoxy, nitro, unhalogenated or partially or fully halogenated $C_1$–$C_2$-alkylenedioxy;
$R^3$ is $C_1$–$C_4$-alkyl which is substituted by phenyl, the alkyl moiety being otherwise unsubstituted and it being possible for the phenyl moiety to have attached to it one to two of the following groups: halogen, cyano, nitro, $C_1$–$C_4$-alkyl, $C_1$–$C_4$-haloalkyl, $C_1$–$C_4$-alkoxy;
$R^4$ is hydrogen.

Compounds I which are especially preferred with a view to the abovementioned biological activity are those compiled in the tables which follow.

(I.1)

Table 1
Compounds of the formula I.1 where
$R^1$=hydrogen;
$R^2$=methyl;
$R^3$=in each case one line of Table A Table 2
Compounds of the formula I.1 where
$R^1$=hydrogen;
$R^2$=fluorine;
$R^3$=in each case one line of Table A Table 3
Compounds of the formula I.1 where
$R^1$=hydrogen;
$R^2$=chlorine;
$R^3$=in each case one line of Table A Table 4
Compounds of the formula I.1 where
$R^1$=hydrogen;
$R^2$=trifluoromethyl;
$R^3$=in each case one line of Table A, with the exception of line No. 1

Table 5
Compounds of the formula I.1 where
$R^1$=methyl;
$R^2$=chlorine;
$R^3$=in each case one line of Table A (I.2)

Table 6
Compounds of the formula I.2 where
$R^1$=hydrogen;
$R^2$=methyl;
$R^3$=in each case one line of Table A Table 7
Compounds of the formula I.2 where
$R^1$=hydrogen;
$R^2$=fluorine;
$R^3$=in each case one line of Table A Table 8
Compounds of the formula I.2 where
$R^1$=hydrogen;

R² = chlorine;
R³ = in each case one line of Table A

Table 9
Compounds of the formula I.2 where
R¹ = hydrogen;
R² = trifluoromethyl;
R³ = in each case one line of Table A, with the exception of line No. 1

Table 10
Compounds of the formula I.2 where
R¹ = methyl;
R² = chlorine;
R³ = in each case one line of Table A

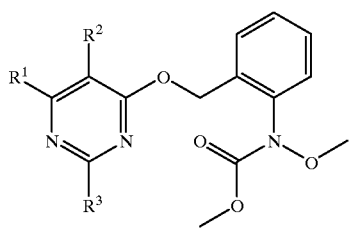

(I.3)

Table 11
Compounds of the formula I.3 where
R¹ = hydrogen;
R² = methyl;
R³ = in each case one line of Table A Table 12
Compounds of the formula I.3 where
R¹ = hydrogen;
R² = fluorine;
R³ = in each case one line of Table A Table 13
Compounds of the formula I.3 where
R¹ = hydrogen;
R² = chlorine;
R³ = in each case one line of Table A Table 14
Compounds of the formula I.3 where
R¹ = hydrogen;
R² = trifluoromethyl;
R³ = in each case one line of Table A, with the exception of line No. 1

Table 15
Compounds of the formula I.3 where
R¹ = methyl;
R² = chlorine;
R³ = in each case one line of Table A

TABLE A

| No. | R³ |
|---|---|
| 1 | H |
| 2 | methyl |
| 3 | ethyl |
| 4 | n-propyl |
| 5 | i-propyl |
| 6 | cyclopropyl |
| 7 | n-butyl |
| 8 | s-butyl |
| 9 | i-butyl |
| 10 | t-butyl |
| 11 | cyclobutyl |
| 12 | n-pentyl |
| 13 | i-pentyl |
| 14 | neo-pentyl |
| 15 | cyclopentyl |
| 16 | n-hexyl |
| 17 | n-heptyl |
| 18 | trifluoromethyl |
| 19 | chloromethyl |
| 20 | O-methyl |
| 21 | O-ethyl |
| 22 | O-n-propyl |
| 23 | O-i-propyl |
| 24 | O-n-butyl |
| 25 | O-s-butyl |
| 26 | O-i-butyl |
| 27 | O-t-butyl |
| 28 | O-n-pentyl |
| 29 | O-i-pentyl |
| 30 | O-neo-pentyl |
| 31 | O-n-hexyl |
| 32 | S-methyl |
| 33 | S-ethyl |
| 34 | S-n-propyl |
| 35 | S-i-propyl |
| 36 | S-n-butyl |
| 37 | S(=O)-methyl |
| 38 | S(=O)-ethyl |
| 39 | S(=O)-n-propyl |
| 40 | S(=O)-i-propyl |
| 41 | S(=O)-n-butyl |
| 42 | S(=O)₂-methyl |
| 43 | S(=O)₂-ethyl |
| 44 | S(=O)₂-n-propyl |
| 45 | S(=O)₂-i-propyl |
| 46 | S(=O)₂-n-butyl |
| 47 | NH₂ |
| 48 | N(methyl)₂ |
| 49 | N(ethyl)₂ |
| 50 | N(n-propyl)₂ |
| 51 | chlorine |
| 52 | O-phenyl |
| 53 | O—CH₂-phenyl |
| 54 | O—CH₂-(4-chlorophenyl) |
| 55 | phenyl |
| 56 | 2-F-phenyl |
| 57 | 3-F-phenyl |
| 58 | 4-F-phenyl |
| 59 | 2-Cl-phenyl |
| 60 | 3-Clphenyl [sic] |
| 61 | 4-Cl-phenyl |
| 62 | 2-Br-phenyl |
| 63 | 3-Br-phenyl |
| 64 | 4-Br-phenyl |
| 65 | 2-methylphenyl |
| 66 | 3-methylphenyl |
| 67 | 4-methylphenyl |
| 68 | 2-CN-phenyl |
| 69 | 3-CN-phenyl |
| 70 | 4-CN-phenyl |
| 71 | 2-OMe-phenyl |
| 72 | 3-OMe-phenyl |
| 73 | 4-OMe-phenyl |
| 74 | 2-CN-phenyl |
| 75 | 3-CN-phenyl |
| 76 | 4-CN-phenyl |
| 77 | 2-nitrophenyl |
| 78 | 3-nitrophenyl |
| 79 | 4-nitrophenyl |
| 80 | 2,4-Cl₂-phenyl |
| 81 | 2,4-(CH₃)₂-phenyl |
| 82 | 3,4-Cl₂-phenyl |
| 83 | 3,4-methylenedioxyphenyl |
| 84 | 3,4-(difluoromethylenedioxy)- |

TABLE A-continued

| No. | R³ |
| --- | --- |
|  | phenyl |
| 85 | 2,4-F₂-phenyl |
| 86 | CH₂-phenyl |
| 87 | CH₂-(3-Cl-phenyl) |
| 88 | CH₂-(4-Cl-phenyl) |
| 89 | 2-CF₃-phenyl |
| 90 | 3-CF₃-phenyl |
| 91 | 4-CF₃-phenyl |

Very especially preferred compounds I amongst those compiled above are those where $R^3$ is not hydrogen.

The compounds I are suitable for controlling harmful fungi and animal pests.

Depending on their chemical and physical properties, they can be formulated with customary formulation auxiliaries, i.e. formulation auxiliaries known to those skilled in the art. The products of this process are termed "compositions".

Examples of suitable formulation auxiliaries are solid or liquid carriers, surfactants and tackifiers.

Liquid carriers are to be understood as meaning liquid solvents such as water and organic solvents, the latter especially acting as an auxiliary solvent if the solvent used is water. Organic solvents which can be used are: aromatics such as xylene, toluene and alkylnaphthalene, chlorinated aromatics or chlorinated aliphatic hydrocarbons such as chlorobenzenes, chloroethylenes and methylene chloride, aliphatic hydrocarbons such as cyclohexane and paraffins, e.g. mineral oil fractions, alcohols such as butanol, iso-butanol, cyclohexanol and glycol, and the corresponding ethers and esters, ketones such as acetone, methyl ethyl ketone, methyl iso-butyl ketone and cyclohexanone, aprotic-dipolar solvents such as dimethylformamide, N-methyl-2-pyrrolidone and dimethyl sulfoxide.

Suitable examples of solid carriers are: ground natural minerals and mineral earths such as silicas, silicates, kaolins, clays, bole, loess, talc, chalk, limestone, lime, dolomite, magnesium oxide, quartz, attapulgite, montmorillonite and diatomeceous earth; ground synthetic minerals such as highly-disperse silica, or meals of synthetic alumina and of synthetic silicates. Examples of solid carriers which are especially suitable for granules are: crushed and fractionated natural rocks such as calcite, marble, pumice, sepiolite; synthetic granules of inorganic and organic meals; granules of organic materials such as sawdust, coconut shells, maize cobs or tobacco stalks.

Suitable surfactants are non-ionic and anionic emulsifiers/foam formers and dispersants:

fatty acid polyoxyethylene esters, such as lauryl alcohol polyoxyethylene ether acetate, alkyl polyoxyethylene ethers or alkyl polyoxypropylene ethers, for example of isotridecyl alcohol and fatty alcohol polyoxyethylene ether, alkylaryl alcohol polyoxyethylene ethers, such as octylphenyl polyoxyethylene ether, tributylphenyl polyoxyethylene ether, ethoxylated iso-octylphenol, octylphenol or nonylphenol or castor oil, sorbitol esters, arylsulfonic acids, alkylsulfonic acids, alkylsulfuric acids, alkali metal, alkaline earth metal and ammonium salts of arylsulfonic acids, eg. ligno-, phenol-, naphthalene- and dibutylnaphthalenesulfonic acid, alkylsulfonic acids, alkylarylsulfonic acids, alkylsulfuric acid, lauryl ether sulfuric acids and fatty alcohol sulfuric acids, fatty acids, sulfated hexa-, hepta- and octadecanols and fatty alcohol glycol ethers, condensates of sulfonated naphthalene and its derivatives with formaldehyde, condensates of naphthalenesulfonic acids with phenol and formaldehyde, protein hydrolysates and in particular as dispersants: lignin-sulfite waste liquors and methylcellulose.

Examples of suitable tackifiers are: carboxymethylcellulose; natural and synthetic polymers in the form of powders, granules or latices, such as gum arabic, polyvinyl alcohol, polyvinyl acetate, natural phospholipids such as cephalins and lecithins, synthetic phospholipids.

The compositions can furthermore comprise one or more representatives of the following groups of substances: colorants, other known active ingredients, trace nutrients and other additives.

Suitable examples of colorants are inorganic pigments such as iron oxide, titanium oxide, Prussian Blue, furthermore organic pigments such as alizarin, azo and metal phthalocyanin colorants. Other known active ingredients are to be understood as meaning, for example, other fungicides and also insecticides, acaricides, herbicides and growth regulators. Trace nutrients are, for example, salts of iron, manganese, boron, copper, cobalt, molybdenum and zinc. Suitable further additives are, for example, mineral and vegetable oils.

Moreover, the compositions can be mixed with other components of practical importance, such as fertilizers or other finished compositions comprising active ingredients.

Depending on the chemical and physical properties of the substances employed, the compositions are prepared in a manner known per se, for example by mixing, concomitant grinding, spraying on, extruding, granulating or dissolving in water, the latter, if required, with the aid of an organic solvent. Powders, materials for spreading and dusts can be obtained, for example, by mixing or concomitantly grinding the compounds I with a solid carrier.

Depending on the substances employed, the compositions are, for example, solutions, emulsions, suspensions, powders, foams, pastes, granules, aerosols or microencapsulations in polymeric substances or in coating compositions for seed.

For use, the compositions which, as a rule, are commercially available as concentrates, are, if required, dissolved, diluted and the like in the customary manner, normally using water in the case of wettable powders, water-dispersible granules, emulsifiable concentrates, dispersions and in some cases also with microgranules. Preparations in the form of dusts and granules, and sprayable solutions, are mostly not diluted further with other inert substances prior to use.

The compositions are applied in a manner known per se, such as by spraying, atomizing, dusting, spreading or pouring. As a rule, the plants are sprayed or dusted with the compositions. Alternatively or additionally, the seeds of the plants are treated in a manner known per se.

Examples of such preparations are:

I. a solution of 90 parts by weight of a compound I according to the invention and 10 parts by weight of N-methyl-2-pyrrolidone, which is suitable for use in the form of microdrops;

II. A mixture of 20 parts by weight of a compound I according to the invention, 80 parts by weight of xylene, 10 parts by weight of the adduct of 8 to 10 mol of ethylene oxide and 1 mol of oleic acid N-monoethanolamide, 5 parts by weight of calcium dodecylbenzenesulfonate, 5 parts by weight of the adduct of 40 mol of ethylene oxide and 1 mol of castor oil: a dispersion is obtained by finely distributing the solution in water;

III. an aqueous dispersion of 20 parts by weight of a compound I according to the invention, 40 parts by weight of cyclohexanone, 30 parts by weight of isobutanol, 20 parts by weight of the adduct of 40 mol of ethylene oxide and 1 mol of castor oil;

IV. an aqueous dispersion of 20 parts by weight of a compound I according to the invention, 25 parts by weight of cyclohexanol, 65 parts by weight of a mineral oil fraction of boiling point 210 to 280° C. and 10 parts by weight of the adduct of 40 mol of ethylene oxide and 1 mol of castor oil;

V. a mixture, ground in a hammer mill, of 80 parts by weight of a compound I according to the invention, 3 parts by weight of sodium diisobutylnaphthalene-1-sulfonate, 10 parts by weight of the sodium salt of a lignosulfonic acid from a sulfite waste liquor and 7 parts by weight of a pulverulent silica gel: a spray mixture is obtained by finely distributing the mixture in water;

VI. an intimate mixture of 3 parts by weight of a compound I according to the invention and 97 parts by weight of finely divided kaolin; this dust comprises 3% by weight of active ingredient;

VII. an intimate mixture of 30 parts by weight of a compound I according to the invention, 92 parts by weight of pulverulent silica gel and 8 parts by weight of paraffin oil which has been sprayed onto the surface of this silica gel; this formulation imparts good adhesion to the active ingredient;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water; this dispersion can be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 68 parts by weight of a paraffinic mineral oil.

If the compounds I are applied as such, it is highly important that they should be finely distributed.

The compounds I and the compositions according to the invention are distinguished by an outstanding activity against a broad spectrum of harmful fungi (phytopathogenic fungi), in particular from the classes of the Ascomycetes,
Basidiomycetes,
Deuteromycetes and
Phycomycetes.

Some of them act systemically and can be employed as foliar- and soil-acting fungicides.

They are especially important for controlling a large number of fungi on a variety of crop plants such as wheat, rye, barley, oats, rice, maize, grass, cotton, soybeans, coffee, sugar cane, grapevines, fruit species, ornamentals and vegetables such as cucumbers, beans and cucurbits, and on the seeds of these plants.

The compounds I, their salts and N-oxides and the compositions according to the invention are applied by treating the harmful fungi, their environment, or the seeds, plants, areas, materials or spaces to be protected against fungal infection, with a fungicidally active amount of the compositions or of the compounds I. Application can be effected before or after infection by the fungi.

Specifically, the compositions according to the invention and the compounds I are suitable for controlling the following plant diseases:

*Erysiphe graminis* (powdery mildew) in cereals, *Erysiphe cichoracearum* and *Sphaerotheca fuliginea* on curcurbits, *Podosphaera leucotricha* on apples, *Uncinula necator* on grapevines, Puccinia species on cereals, Rhizoctonia species on cotton, rice and lawns, Ustilago species on cereals and sugar cane, *Venturia inaequalis* (scab) on apples, Helminthosporium species on cereals, *Septoria nodorum* on wheat, *Botrytis cinerea* (gray mold) on strawberries, grapevines, ornamentals and vegetables, *Cercospora arachidicola* on peanuts, *Pseudocercosporella herpotrichoides* on wheat, barley, *Pyricularia oryzae* on rice, *Phytophthora infestans* on potatoes and tomatoes, Fusarium and Verticillium species on a variety of plants, *Plasmopara viticola* on grapevines, Pseudoperonospora species in hops and cucumbers, Alternaria species on vegetables and fruit.

In general, the fungicidal compositions comprise from 0.1 to 95, preferably from 0.5 to 90, % by weight of active ingredient.

Depending on the nature of the desired effect, the application rates are from 0.01 to 2.0 kg of active ingredient per ha.

In the case of seed treatment, amounts of from 0.001 to 0.1 g, preferably 0.01 to 0.05 g, of active ingredient are generally required per kilogram of seed.

In the use form as fungicides, the compositions according to the invention can also be present together with other active ingredients, eg. with herbicides, insecticides, growth regulators, fungicides or else with fertilizers.

A mixture with fungicides frequently results in a widened fungicidal spectrum of action.

The following list of fungicides in conjunction with which the compounds according to the invention can be used is intended to illustrate the possible combinations, but not to impose any limitation:

sulfur, dithiocarbamates and their derivatives such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethyl-thiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives such as dinitro(1-methylheptyl) phenylcrotonate, 2-sec-butyl-4,6-dinitrophenyl-3,3-dimethylacrylate, 2-sec-butyl-4,6-dinitrophenyl isopropylcarbonate, diisopropyl 5-nitroisophthalate;

heterocyclic substances such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)-phosphinyl]-3-phenyl-1,2,4-triazole, 2,3-dicyano-1,4-dithioanthraquinone, 2-thio-1,3-dithiolo-[4,5-b]-quinoxaline, methyl 1-(butylcarbamoyl)-2-benzimidazolecarbamate, 2-methoxy-carbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfo-diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-mercapto-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine-4,4-dioxide, 2-methyl-5,6-dihydro-4H-pyran-3-carboxanilide, 2-methylfuran-3-carboxanilide, 2,5-dimethyl-furan-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butyl-phenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolyl-urea, 1-(4-chloro-phenoxy)-3,3-dimethyl-1-(1H-1,2,4-triazol-1-yl)-2-butanone, (2-chlorophenyl)-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)-benzene, 1,2-bis(3-methoxycarbonyl-2-thioureido)-benzene, [2-(4-chlorophenyl)ethyl]-(1,1-dimethylethyl)-1H-1,2,4-triazol-1-ethanol and a variety of fungicides such as dodecylguanidine acetate, 3-[3-(3,5-dimethyl-2-oxycyclohexyl)-2-hydroxyethyl)] glutarimide [sic], hexachlorobenzene, DL-methyl-N-(2,6-dimethylphenyl)-N-2-furoylalaninate, DL-N-(2,6-dimethylphenyl)-N-(2'-methoxy-acetyl)alanine methyl ester, N-(2,6-dimethylphenyl)-N-chloro-acetyl-D,L-2-aminobutyrolactone, DL-N-(2,6-dimethylphenyl)-N-(phenylacetyl)alanine methyl ester, 5-methyl-5-vinyl-3-(3,5-di-chlorophenyl)-2,4-dioxo-1,3-oxazolidine,-3-[3,5-dichlorophenyl-(5methyl)5-methoxymethyl]-1,3-oxazolidine-2,4-dione-2,4-, 3-(3,5-dichlorohenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-a-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis-(4-fluorophenyl)-methylsilyl)methyl)-1H-1,2,4-triazole, strobilurins such as methyl E-methoximino-[α-(o-tolyloxy)-o-tolyl]acetate, methyl E-2-{2-[6-(2-cyanophenoxy)pyrimidin-4-yloxy]phenyl}-3-methoxyacrylate, methyl E-methoximino-[a-(2-phenoxyphenyl)]acetamide, methyl E-methoximino-[a-(2,5-dimethylphenoxy)-o-tolyl]acetamide, anilinopyrimidines such as N-(4,6-dimethylpyrimidin-2-yl)aniline, N-[4-methyl-6-(1-propynyl)pyrimidin-2-yl] aniline, N-(4-methyl-6-cyclopropyl-pyrimidin-2-yl)aniline, phenylpyrroles such as 4-(2,2-difluoro-1,3-benzodioxol-4-yl)-pyrrole-3-carbonitrile, cinnamamides such as 3-(4-chlorophenyl)-3-(3,4-dimethoxy-phenyl)acryloylmorpholine, and (2RS,3SR)-1-[3-(2-chlorophenyl)-2-[4-fluorophenyl] oxiran-2-ylmethyl]-1H-1,2,4-triazole.

Moreover, the compounds of the formula I are suitable for the efficient control of animal pests, especially from the classes of the insects, arachnids and nematodes. They can be employed as pesticides in crop protection and in the hygiene, stored-product and veterinary sectors.

The harmful insects include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor,*

*Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the heteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the homopterans (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, arachnids (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root knot nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The concentrations of active ingredient in the ready-to-use preparations can be varied within substantial ranges. Im general, they are from 0.0001 to 10%, preferably from 0.01 to 1%.

The active ingredients can also be used successfully in the ultra-low volume method (ULV), it being possible to apply formulations comprising more than 95% by weight of active ingredient, or even the active ingedient without additives.

The application rate of active ingredient for controlling pests is 0.1 to 2.0, preferably 0.2 to 1.0 kg/ha under open conditions.

SYNTHESIS EXAMPLES

The protocols given in the synthesis examples below can be used for obtaining other representatives of the compounds I or III by modifying the starting compounds. The physical data of the products prepared accordingly are shown in the tables which follow in each case.

The chemical shifts (in ppm) of the $^1$H NMR spectra was measured against tetramethylsilane (br=broad signal, s=singulet, d=doublet, m=multiplet).

I) Preparation of compounds I in which Q is $C(=NOCH_3)$—$CONHCH_3$. For example, the starting compounds III can be prepared as described below (Examples 1 to 3) from methyl E-2-methoxyimino-2-[(2-methylphenyloxymethyl)phenyl]acetate, which is readily accessible, (cf. EP-A 493 711) by means of an aminolysis with methylamine, followed by cleavage with boron trichloride or hydrogen bromide.

Example 1

N-Methyl-E-2-methoxyimino-2-[(2-methylphenyloxymethyl)phenyl]-acetamide 250 g of methyl E-2-methoxyimino-2-[(2-methylphenyloxymethyl)-phenyl]acetate were suspended in 1 l of 40% strength aqueous methylamine solution, and the suspension was heated for 4 hours at 40° C. After the mixture had been cooled to room temperature (20° C.), the solid was filtered off with suction, washed repeatedly with water and dried at 50° C. This gave 229.8 g of the title compound as colorless crystals.

m.p.: 109–112° C.; $^1$H NMR (CDCl$_3$): 2.20 (s, 3H); 2.85 (d, 3H); 3.95 (s, 3H); 4.90 (s, 2H); 6.7 (NH); 6.8 –7.6 (m, 8H)

Example 2

N-Methyl-E-2-methoxyimino-2-[(2-chloromethyl)phenyl]acetamide 2 g of N-Methyl-E-2-methoxyimino-2-[(2-methylphenyloxymethyl)-phenyl]acetamide of Example 1 were introduced into 30 ml of anhydrous dichloromethane at 10° C. 9.4 g of boron trichloride (as a 1-molar solution in n-hexane) were added dropwise, the mixture was refluxed for 1.5 hours and cooled to 10° C., a further 9.4 g of boron trichloride were added, and the mixture was stirred overnight at room temperature (20° C.). After 8.2 g of methanol had been added dropwise, the batch was evaporated on a rotary evaporator. The residue was taken up in 100 ml of dichloromethane and washed with 5% sodium hydroxide solution and then with water. The organic phase was subsequently dried over sodium sulfate. After the solvent had been stripped off, there remained 1.2 g of the title compound as an oil.

$^1$H NMR (CDCl$_3$): 2.95 (d, 3H); 3.90 (s, 3H); 4.45 (s, 2H); 6.8 (NH); 7.1–7.6 (m, 4H)

Example 3

N-Methyl-E-2-methoxyimino-2-[(2-bromomethyl)phenyl]acetamide 10 g of N-methyl-E-2-methoxyimino-2-[(2-methylphenyloxymethyl)-phenyl]acetamide of Example 1 were introduced into 50 ml of anhydrous dichloromethane. Hydrogen bromide was passed into the solution until saturation point was reached (approximately 9 g of HBr). After the mixture had been stirred for 68 hours at room temperature, all of the starting material was reacted. After a further 50 ml of dichloromethane had been added, the mixture was worked up as in Example 2. There remained 7.0 g of the title compound as an oil which crystallized upon standing.

m.p.: 128–129° C.; $^1$H NMR (CDCl$_3$): 2.95 (d, 3H); 3.95 (s, 3H); 4.35 (s, 2H); 6.85 (NH); 7.1–7.5 (m, 4H)

Example 4

N-Methyl-E-2-methoxyimino-2-[(2-[2-n-propyl-5-methylpyrimidin-4-yl)]oxy-methyl)phenyl]acetamide 1.52 g of 2-n-propyl-5-methyl-4-hydroxypyrimidine were dissolved in 25 ml of dimethylformamide. 1.38 g of finely pulverulent potassium carbonate and 2.85 g of N-methyl-E-2-methoxyimino-2-[(2-bromomethyl)phenyl]acetamide were added. The mixture was stirred for 4 hours at 50° C. and concentrated. The residue was taken up in 300 ml of half-concentrated aqueous sodium chloride solution and extracted three times with in each case 100 ml of methyl tert-butyl ether. The combined organic phases were then washed with water and dried over sodium sulfate. After the solvent had been stripped off, the residue which remained was chromatographed on silica gel with cyclohexane/ethyl acetate 1:2. This gave 0.6 g of the title compound as a colorless solid.

m.p.: 60–62° C.

TABLE S1

| No. | R$^1$ | R$^2$ | R$^3$ | R$^4$ | Physical data (m.p. [° C.]; IR [cm$^{-1}$]) |
|---|---|---|---|---|---|
| 1 | H | methyl | methyl | H | 136–137 |
| 2 | H | methyl | ethyl | H | 105–107 |
| 3 | H | methyl | n-propyl | H | 60–62 |
| 4 | H | methyl | cyclopropyl | H | 128–130 |
| 5 | H | methyl | cyclohexyl | H | 1673, 1593, 1564, 1525, 1450, 1428, 1319, 979. |
| 6 | H | methyl | iso-propyl | H | 70–72 |
| 7 | methyl | chlorine | n-propyl | H | 73–74 |
| 8 | methyl | chlorine | cyclohexyl | H | 96–97 |
| 9 | H | methyl | n-butyl | H | 1671, 1594, 1565, 1525, 1459, 1427, 1315, 1037, 1020. |
| 10 | H | methyl | n-pentyl | H | 1671, 1594, 1565, 1525, 1459, 1427, 1317, 1038, 979. |
| 11 | H | methyl | n-hexyl | H | 1671, 1594, 1565, 1525, 1459, 1427, 1316, 1038, 979. |
| 12 | H | methyl | tert-butyl | H | 80–82 |
| 13 | H | methyl | phenyl | H | 135–136 |
| 14 | H | methyl | 4-Cl-phenyl | H | 165–166 |
| 15 | H | chlorine | n-propyl | H | 69–71 |
| 16 | H | chlorine | methyl | H | 125–126 |
| 17 | H | chlorine | ethyl | H | 94–96 |
| 18 | H | chlorine | n-butyl | H | 73–75 |
| 19 | H | chlorine | n-pentyl | H | resin |
| 20 | H | chlorine | phenyl | H | 159–161 |

II) Preparation of compounds I where Q is C(=NOCH$_3$)-COOCH$_3$.

Example 5

Methyl E-2-methoxyimino-2-[(2-[2-ethyl-5-methylpyrimidine-4-yl)]oxy-methyl)phenyl]acetate (Table No. 2)

2.17 g of 2-ethyl-5-methyl-4-hydroxypyrimidine were dissolved in 40 ml of dimethylformamide. 3.1 g of finely pulverulent potassium carbonate and 4.29 g of methyl E-2-methoxyimino-2-[(2-bromo-methyl)phenyl]acetate were added to this solution. The mixture was stirred for four hours at 50° C. and then overnight at room temperature and concentrated. The residue was taken up in 300 ml of dilute sodium chloride solution and extracted three times with methyl tert-butyl ether. The combined organic phases were first washed with sodium hydrogen carbonate solution and then with water. The combined organic phases were then dried over sodium sulphate. After the solvent had been stripped off, the residue which remained was recrystallized from n-hexane/methyl tert-butyl ether. This gave 1.3 g of the title compound as a colorless solid.

m.p.: 75–77° C.

TABLE S2

[Structure showing pyrimidine with R¹, R², R³ substituents connected via O-CH₂ to phenyl ring with R⁴ substituent, bearing C(=NOCH₃)COOCH₃ group]

| No. | R¹ | R² | R³ | R⁴ | Physical Data m.p. [° C.], IR [cm⁻¹] |
|---|---|---|---|---|---|
| 1 | H | methyl | methyl | H | 97–99 |
| 2 | H | methyl | ethyl | H | 75–77 |
| 3 | H | methyl | n-propyl | H | 58–60 |
| 4 | H | methyl | cyclopropyl | H | 88–89 |
| 5 | H | methyl | cyclohexyl | H | 70–72 |
| 6 | H | methyl | i-propyl | H | 52–53 |
| 7 | methyl | chlorine | n-propyl | H | 61–74 |
| 8 | methyl | chlorine | cyclohexyl | H | 109–115 |
| 9 | H | methyl | n-butyl | H | 1729, 1594, 1565, 1457, 1428, 1318, 1218, 1069, 1019. |
| 10 | H | methyl | n-pentyl | H | 1729, 1594, 1565, 1457, 1428, 1319, 1218, 1069, 1019. |
| 11 | H | methyl | n-hexyl | H | 62–64 |
| 12 | H | methyl | tert-butyl | H | 74–75 |
| 13 | H | methyl | phenyl | H | 120–122 |
| 14 | H | methyl | 4-Cl-phenyl | H | 133–134 |
| 15 | H | chlorine | n-propyl | H | 67–69 |
| 16 | H | chlorine | methyl | H | 105–106 |
| 17 | H | chlorine | ethyl | H | 81–83 |
| 18 | H | chlorine | n-butyl | H | 53–55 |
| 19 | H | chlorine | n-pentyl | H | 66–67 |
| 20 | H | chlorine | phenyl | H | 145–146 |

Use Examples

1. Example of the Activity Against Harmful Fungi

The following experiments on the fungicidal activity of the compounds I were carried out with an emulsion composed of 10% by weight of the active ingredient and of 90% by weight of a mixture of 70% by weight of cyclohexanol, 20% by weight of Nekanil® LN (Lutensol® AP6, wetting agent with emulsifying and dispersant action based on ethoxylated alkylphenols) and 10% by weight of Uniperol® EL (nonionic emulsifier based on ethoxylated castor oil).

The desired concentrations of active ingredient were adjusted by diluting this emulsion with water.

Activity against Pyricularia oryzae (protective)

Leaves of rice seedlings cv. "Tai-Nong 67" in pots were sprayed to runoff point with aqueous emulsions comprising 80% of active ingredient and 20% of emulsifier in the dry matter and, 24 hours later, inoculated with an aqueous spore suspension of Pyricularia oryzae. The test plants were subsequently placed in controlled-environment cabinets at 22–24° C. and an atmospheric humidity of 95–99%. The extent of disease was determined visually after 6 days.

The following compounds according to the invention were tested in each case alone in the form of an aqueous preparation comprising 63 ppm of the active ingredient in question: Nos. 1, 3, 5, 6, 7, 8, 9, 10 and 11 of Table S1. When applying these compounds, visual assessment revealed fungal infection on 0 to 5% of the leaf areas. The infection level of untreated plants was 80%.

2. Examples of the Activity Against Animal Pests

The activity of the compounds of the formula I against animal pests was demonstrated by the following experiments:

The active ingredients were formulated a) as an 0.1% strength solution in acetone or b) as a 10% emulsion in a mixture 70% by weight of cyclohexanone, 20% by weight of Nekanil® LN (Lutensol® AP6, wetting agent with emulsifying and dispersant action based on ethoxylated alkylphenols) and 10% by weight of Uniperol® EL (nonionic emulsifier based on ethoxylated castor oil)

and diluted to give the desired concentration, using acetone in the case of a) and water in the case of b).

After the experiments had been concluded, in each case the lowest concentration at which the compounds still caused an 80–100% inhibition or mortality in comparison with untreated control experiments were determined (limit or minimum concentration).

We claim:

1. A 2-(O-[pyrimidin-4-yl]oxymethylene)phenylacetic acid compound of formula I

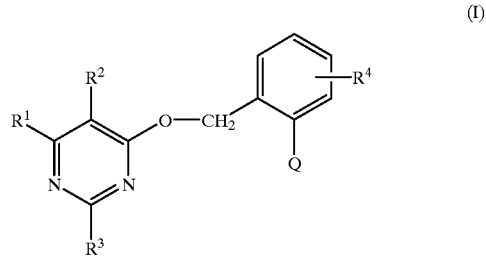

or a salt or N-oxide thereof wherein

R¹ is hydrogen or C₁–C₄-alkyl;

R² is halogen or C₁–C₂-alkyl;

R³ is C₁–C₈-alkyl, it being possible for the alkyl radicals to have attached to them a phenyl group which, in turn, can have attached to it one or, independently of one another, two of the following substituents: halogen, cyano, nitro, C₁–C₄-alkyl, C₁–C₄-haloalkyl and C₁–C₄-alkoxy; or is C₁–C₈-haloalkyl; or is phenyl which is unsubstituted or substituted;

R₄ is hydrogen; cyano; halogen; C₁–C₄-alkyl; C₁–C₄-haloalkyl or C₁–C₄-alkoxy; and Q is C(=NOCH₃)—CONHCH₃ or C(=NOCH₃)—COOCH₃.

2. A composition which is suitable for controlling harmful fungi and animal pests, comprising an effective amount of the compound of formula I or its salt or N-oxide defined in claim 1 and at least one formulation auxiliary.

3. A process for the preparation of the composition defined in claim 2, which comprises processing the compound of formula I with at least one formulation auxiliary.

4. A method of controlling harmful fungi and animal pests, which comprises treating the harmful fungi or the animal pests, their environment, or plants, seeds, areas, materials or spaces to be kept free from them, with an effective amount of the compound of formula I defined in claim 1, or a salt or N-oxide thereof.

5. The compound of formula I defined in claim 1, or its salt or N-oxide, wherein R¹ is C₁–C₄-alkyl.

6. The compound of formula I defined in claim 1, or its salt or N-oxide, wherein $R^1$ is hydrogen or methyl.

7. The compound of formula I defined in claim 1, or its salt or N-oxide, wherein $R^2$ is halogen.

8. The compound of formula I defined in claim 1, or its salt or N-oxide, wherein $R^2$ is fluoro or chloro.

9. The compound of formula I defined in claim 1, or its salt or N-oxide, wherein $R^1$ is $C_1$–$C_4$-alkyl and $R^2$ is halogen.

10. The compound of formula I defined in claim 1, or its salt or N-oxide, wherein $R^3$ is $C_1$–$C_8$-alkyl, or is phenyl which is unsubstituted or substituted.

11. The compound of formula I defined in claim 1, or its salt or N-oxide, wherein $R^3$ is $C_1$–$C_8$-alkyl which is unsubstituted or partially or fully halogenated.

12. The compound of formula I defined in claim 1, or its salt or N-oxide, wherein $R^4$ is hydrogen.

13. The compound of formula I defined in claim 1, or its salt or N-oxide, wherein Q is C(=NOCH$_3$)—CONHCH$_3$.

14. The compound of formula I defined in claim 1, or its salt or N-oxide, wherein wherein Q is C(=NOCH$_3$)—CO$_2$CH$_3$.

15. The compound of formula I defined in claim 1 or its salt or N-oxide, wherein $R^2$ is halogen or methyl.

16. The compound of formula I defined in claim 1 or its salt or N-oxide, wherein $R^3$ is $C_1$–$C_8$-alkyl, or is phenyl which is unsubstituted or carries one to three radicals selected from the group consisting of cyano, nitro, trifluoromethyl, halogen, $C_1$–$C_4$-alkyl, $C_1$–$C_4$-alkoxy, $C_1$–$C_2$-alkylenedioxy and $C_1$–$C_2$-haloalkylenedioxy.

17. The compound of formula I defined in claim 10 or its salt or N-oxide, wherein $R^1$ is hydrogen or methyl.

18. The compound of formula I defined in claim 10 or its salt or N-oxide, wherein $R^2$ is halogen or methyl.

19. The compound of formula I defined in claim 10 or its salt or N-oxide, wherein $R^4$ is hydrogen.

* * * * *